United States Patent [19]

Nakai et al.

[11] Patent Number: 4,668,457

[45] Date of Patent: May 26, 1987

[54] METHOD OF MAKING STANDARD MARBLING MODELS USED FOR JUDGING AND GRADING BEEF

[75] Inventors: Hiroyasu Nakai, Matsudo; Toshio Ikeda, Ibaragi; Shiro Ando, Ibaragi; Kyohei Ozutsumi, Ibaragi, all of Japan

[73] Assignee: National Institute of Animal Industry, Ibaragi, Japan

[21] Appl. No.: 843,339

[22] Filed: Mar. 24, 1986

[30] Foreign Application Priority Data

Apr. 30, 1985 [JP] Japan ................... 60-93297

[51] Int. Cl.$^4$ .............. B29C 33/40; B29C 33/42; B29C 39/10; B44F 9/00
[52] U.S. Cl. .................... 264/227; 264/138; 264/247; 428/15
[58] Field of Search ............ 264/219, 227, 245, 247, 264/138; 428/15, 16

[56] References Cited

U.S. PATENT DOCUMENTS

| | | | |
|---|---|---|---|
| 1,137,595 | 4/1915 | Eyl | 264/247 |
| 1,776,622 | 9/1930 | Errington et al. | 264/227 |
| 2,651,079 | 9/1953 | Michaelson et al. | 264/219 |
| 3,472,306 | 10/1986 | Austin et al. | 264/227 |
| 3,487,134 | 12/1969 | Burr | 264/219 |
| 3,739,051 | 6/1973 | Smith | 264/219 |
| 3,917,786 | 11/1975 | Weigert | 264/227 |
| 3,949,502 | 4/1976 | Carr | 428/15 |
| 4,073,854 | 2/1978 | Burry | 264/247 |

FOREIGN PATENT DOCUMENTS 0138463 12/1978 Japan ................... 264/247

Primary Examiner—Jan H. Silbaugh
Assistant Examiner—Jeremiah Durkin, II
Attorney, Agent, or Firm—Martin A. Farber

[57] ABSTRACT

Resin pieces having a fat color corresponding to fat meats are molded and placed in a female mold. Resin having a lean meat color is pured in the female mold, and solidified resin is taken out from the mold.

2 Claims, 1 Drawing Figure

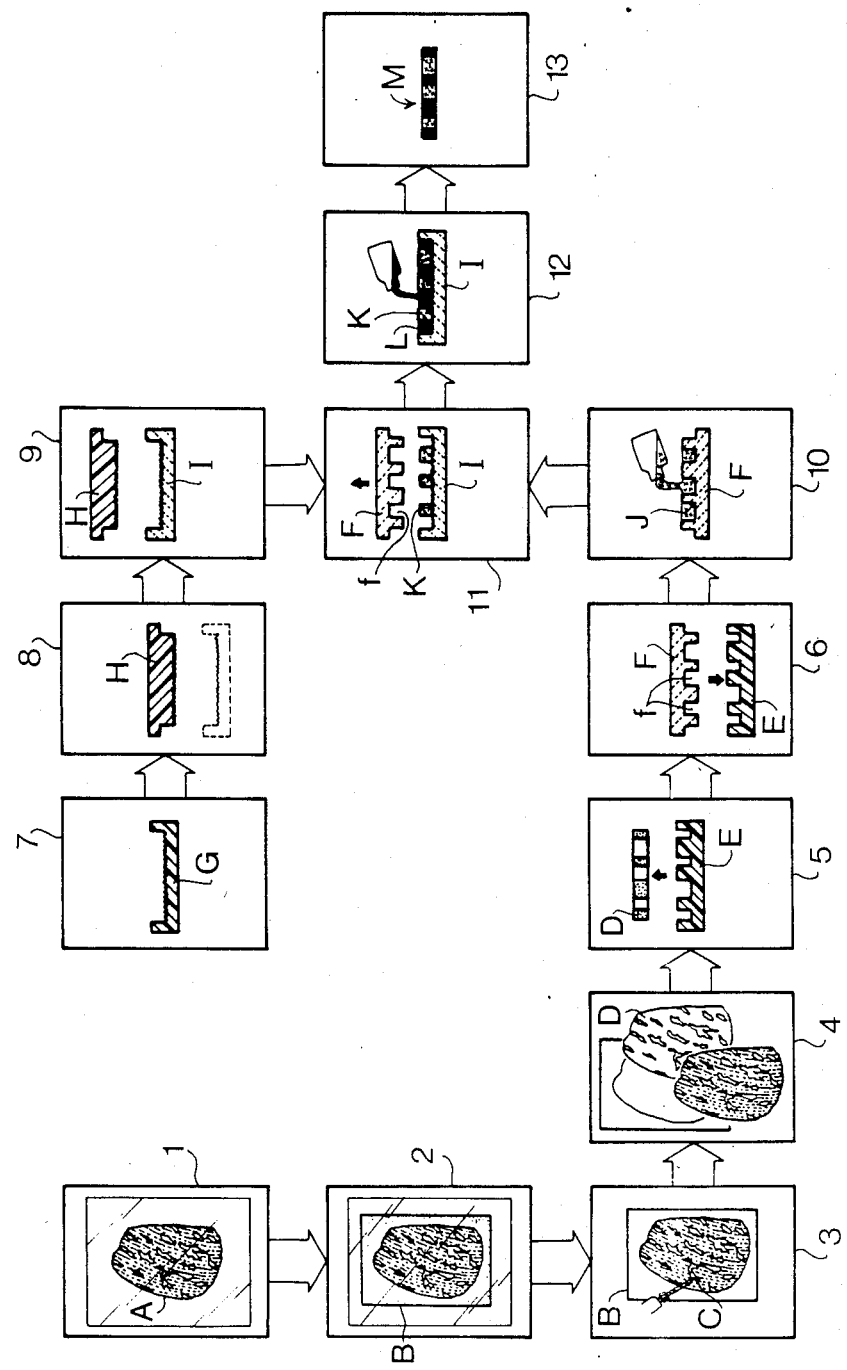

METHOD OF MAKING STANDARD MARBLING MODELS USED FOR JUDGING AND GRADING BEEF

BACKGROUND OF THE INVENTION

The present invention relates to a method for producing standard models used for judging and grading beef in accordance with marbling thereof.

Conventionally, Japan Meat Grading Association has provided pictures illustrating six grades of marbling of beef which have been used for judging and grading beef marbling. However, these pictures can not actually be used to be compared with beef when grading beef, but in real, the grading of beef has been carried out depending on subjective decision of a judge.

SUMMARY OF THE INVENTION

Therefore, the object of the present invention is to provide a method for producing standard models used for judging and grading beef in its natural size which can be compared with beef when judging and grading. These standard models are based on six kinds of photographs, corresponding to the six grades, provided by Japan Meat Grading Association.

In accordance with the present invention, there is provided a method comprising; duplicating a positive meat picture on a plaster board, carving the plaster board at portions corresponding to fat meats to form grooves, cutting the plaster board into a shape of a specimen, molding a first female mold from the plaster, molding a first male mold from the first female mold, making a second male mold having a surface resembling a surface of meat, molding a second female mold from the second male mold with soft polyester, shape of which corresponds to the first mole mold, molding resin pieces having a fat color by grooves on the first male mold, putting the pieces in the second female mold, pouring resin having a lean meat color in the second female mold, and taking out a solidified resin from the second female.

The other objects and features of this invention will be apparently understood from the following description with reference to the accompanying drawings.

BRIEF DESCRIPTION OF DRAWINGS

Single FIGURE is a block diagram showing a method of the present invention.

DETAILED EXPLANATION OF PREFERRED EMBODIMENT

The method for producing a standard marbling model for judging and grading beef will be explained with reference to the block diagram. At a step 1, a positive meat picture A having a substantially same size as a specimen of beef is printed from a standard negative picture. The positive meat picture is duplicated on a plaster board B at a step 2. At a step 3, portions C corresponding to fat meats of the plaster board B are carved with sculpture knives and needles. Then the plaster board is cut to produce a piece of board D of the meat picture A at a step 4. Further the board D is made into thin plate having a thickness of 1.5 cm. At a step 5, a female mold E of silicon resin is molded from the board D, and then a male mold F is molded at a step 6. Thus, the mold F has grooves f corresponding to fat portions C.

On the other hand, at a step 7, another female mold G having an irregular surface resembling a surface of a meat is made of silicon resin and a male mold H of a size corresponding to the female mold E, having 1 cm thickness, is molded. Further, another female mold I of soft polyester is molded at a step 9, which corresponds to the male mold F. In the grooves f, silicon resin J including 10% (weight) of ethyrole (3:1 in volume), hardener (CAT-108) and hardening accelerator (CAT-RS), and having a fat color is poured at a step 10. Solidified resin pieces K having a fat color are transferred in the female mold I at a step 11. At a step 12, silicon resin L colored by pigment in lean meat color is poured in the female mold I and a solidified model M is taken out at a step 13. Thus, a standard model M having fat and lean meat colors is made-up.

Such standard marbling models in six grades are made up for grading beef.

In accordance with the method of the present invention, it enables to make standard models having delicately different colored and marbled beef depending on the mixture of material. Accordingly, proper and exact judgement and grading of beef can be performed.

While the presently referred embodiment of the present invention has been shown and described, it is to be understood that this disclosure is for the purpose of illustration and that various changes and modifications may be made without departing from the scope of the invention as set forth in the appended claims.

What is claimed is:

1. A method of making a standard model for judging and grading beef, which comprises:
    duplicating a positive meat picture on a plaster board;
    carving the plaster board at portions corresponding to fat portions of the meat to form grooves;
    cutting the plaster board into a shape of a specimen including the grooves;
    molding a first female mold from the plaster board specimen;
    molding a first male mold including grooves corresponding to the fat portions from the first female mold;
    making a second male mold having a surface resembling a surface of the meat;
    molding a second female mold from the second male mold with soft polyester, which shape corresponds to the first male mold;
    molding resin pieces having a fat color by the grooves on the first male mold;
    putting the pieces in the second female mold;
    pouring resin having a lean meat color in the second female mold; and
    taking out a solidified resin forming the standard model from the second female.

2. The method according to claim 1 wherein the first and second male and female molds are made of silicon resin.

* * * * *